United States Patent
Osorio et al.

[11] Patent Number: 5,989,029
[45] Date of Patent: Nov. 23, 1999

[54] CUSTOMIZED DENTAL ABUTMENTS AND METHODS OF PREPARING OR SELECTING THE SAME

[75] Inventors: Julian Osorio, Waban; Andrew Ziegler, Arlington, both of Mass.

[73] Assignee: Atlantis Components, Inc., Cambridge, Mass.

[21] Appl. No.: 08/960,046

[22] Filed: Oct. 29, 1997

Related U.S. Application Data

[60] Provisional application No. 60/051,957, Jul. 8, 1997.

[51] Int. Cl.⁶ ........................... A61C 8/00
[52] U.S. Cl. ........................... 433/173; 433/223
[58] Field of Search ................ 433/172, 173, 433/174, 175, 213, 214, 223

[56] References Cited

U.S. PATENT DOCUMENTS

| | | | |
|---|---|---|---|
| 4,681,542 | 7/1987 | Baum | 433/172 |
| 4,955,811 | 9/1990 | Lazzara et al. | 433/173 |
| 4,988,297 | 1/1991 | Lazzara et al. | 433/173 |
| 5,052,929 | 10/1991 | Seal | 433/173 |
| 5,104,318 | 4/1992 | Piche et al. | 433/174 |
| 5,106,300 | 4/1992 | Voitik | 433/173 |
| 5,125,839 | 6/1992 | Inger et al. | 433/169 |
| 5,180,303 | 1/1993 | Hornburg et al. | 433/173 |
| 5,193,999 | 3/1993 | Staubli | 433/72 |
| 5,213,502 | 5/1993 | Daftary | 433/172 |
| 5,273,429 | 12/1993 | Rekow et al. | 433/223 |
| 5,297,963 | 3/1994 | Dafatry | 433/172 |
| 5,334,024 | 8/1994 | Niznick | 433/173 |
| 5,338,196 | 8/1994 | Beaty et al. | 433/172 |
| 5,362,235 | 11/1994 | Daftary | 433/172 |
| 5,362,237 | 11/1994 | Chalifoux | 433/220 |
| 5,382,164 | 1/1995 | Stern | 433/213 |
| 5,417,568 | 5/1995 | Giglio | 433/173 |
| 5,419,702 | 5/1995 | Beaty et al. | 433/214 |
| 5,447,435 | 9/1995 | Brodbeck | 433/173 |
| 5,476,383 | 12/1995 | Beaty et al. | 433/214 |
| 5,492,471 | 2/1996 | Singer | 433/172 |
| 5,497,336 | 3/1996 | Andersson et al. | 364/474.03 |
| 5,527,182 | 6/1996 | Willoughby | 433/172 |
| 5,571,015 | 11/1996 | Siegmund | 433/173 |
| 5,651,675 | 7/1997 | Singer | 433/173 |
| 5,658,147 | 8/1997 | Phimmasone | 433/213 |
| 5,662,476 | 9/1997 | Ingber et al. | 433/213 |
| 5,667,384 | 9/1997 | Sutter et al. | 433/173 |
| 5,674,069 | 10/1997 | Osorio | 433/172 |
| 5,674,073 | 10/1997 | Ingber et al. | 433/213 |
| 5,685,715 | 11/1997 | Beaty et al. | 433/173 |
| 5,688,123 | 11/1997 | Meiers et al. | 433/173 |
| 5,779,480 | 7/1998 | Groll et al. | 433/173 |

FOREIGN PATENT DOCUMENTS

| | | | |
|---|---|---|---|
| 0 477 644 A1 | 4/1992 | European Pat. Off. | |
| 2634369 | 1/1990 | France | 433/174 |
| WO 96/34576 | 11/1996 | WIPO | |
| WO 97/37610 | 10/1997 | WIPO | |

OTHER PUBLICATIONS

Wheeler, Russell C., "Nomenclature and General Considerations," (*Dental Anatomy, Physiology and Occlusion*, 5th Edition, 1974), pp. 3–23.

*Primary Examiner*—Ralph A. Lewis
*Attorney, Agent, or Firm*—Testa, Hurwitz & Thibeault, LLP

[57] ABSTRACT

A customized dental abutment is provided which replicates a tooth being replaced. The dimensions of the abutment are determined by a computer algorithm that modifies standard tooth type models according to a series of measurements taken of the site of desired tooth replacement. Methods of the invention relate to taking a series of measurements of the site of desired tooth replacement, determining the type of tooth being replaced, and preparing or selecting a customized dental abutment based on the measurements and determination. The preparation or selection is made by modifying standard measurements for the type of tooth being replaced in conformity with the measurements taken of the site of desired tooth replacement.

3 Claims, 12 Drawing Sheets

CUSTOMIZED DENTAL ABUTMENTS AND METHODS OF PREPARING OR SELECTING THE SAME

This application claims priority to U.S. Provisional Application Ser. No. 60/051,957 filed Jul. 8, 1997.

FIELD OF THE INVENTION

The invention relates to customized dental abutments and methods of preparing or selecting such abutments. More specifically, the invention relates to customized dental abutments fabricated through the use of a computer algorithm into which a series of measurements taken of the site for tooth replacement are entered.

BACKGROUND OF THE INVENTION

Dental restorative systems seek to provide cosmetic and functional replacements for missing teeth. A dental restorative system that replaces a single tooth typically includes three components. These are the dental implant fixture, the abutment, and the crown. The dental implant fixture anchors the restorative system to the jawbone. The crown replicates the contour and appearance of the visible portion of the restorative system to match that of the natural dentition. Finally, the abutment connects the crown to the dental implant fixture. The abutment also holds the crown in proper alignment relative to the implant fixture, and absorbs the stress of chewing. A customized abutment should also match the size, shape and contour of the original tooth in order to provide the best possible appearance.

Standard methods for preparing dental restorative systems require considerable time, labor, and expense. Methods typically require that the patient make between six and ten visits to the dentist's office to complete installation of the restorative system. An oral surgeon or periodontist is required to surgically implant the dental implant fixture into the patient's jawbone. A general dentist or prosthodontist typically performs the measurement and fitting of the abutment and crown, and a technician typically sculpts the abutment and crown.

During the first office visit, an impression of the patient's existing teeth is made. During the second visit, the dental implant fixture is installed in the patient's jawbone. At the third visit, a temporary healing abutment is installed in the implant fixture. After healing, a fourth visit is necessary to make an impression of the patient's mouth showing the position of the implant fixture relative to the natural dentition. From this impression, a customized abutment is fabricated. At a fifth visit, the abutment is installed along with a temporary crown. At the sixth visit, the progress of gum healing is examined and a final impression of the patient's mouth is made in order to determine if the abutment needs to be further modified. At the seventh visit, the crown is installed. The number of office visits required increases if the abutment or crown needs to be modified before installation of the final crown.

The standard procedure therefore requires a considerable number of visits to the dentist's office for the patient and the labor of up to three different dental professionals. This time and labor adds to the high cost of undergoing a tooth replacement by this method. Accordingly, there remains a need in the art for a methods and materials that will aid in reducing the time, labor and cost of dental implant restorations. The present invention addresses this need by presenting customized dental abutments and methods of preparing or selecting such abutments in a manner which is quicker and less costly than standard techniques.

SUMMARY OF THE INVENTION

Dental abutments of the present invention are customized to replicate a tooth being replaced. A series of measurements of the tooth site is taken, including measurements of the mesial-distal angle, the facial-lingual angle, the rotational axis of a dental implant fixture implanted at the site of desired tooth replacement, the width, the facial-lingual offset, the mesial-distal offset, and the height from the gumline to the top of a dental implant fixture. In addition to these measurements, a determination of the tooth type (e.g., lateral incisor, first bicuspid, etc.) is made. Additional measurements may include the height to the occlusal plane and the gingival profile of the tooth being replaced. The dimensions, including the size, position, orientation and inclination, of the adjacent and opposing teeth may also be made.

According to the invention, an abutment is customized by entering measurements into an algorithm that modifies a standard tooth shape for the type of tooth being replaced. The result is a customized abutment that regulates characteristics of the tooth being replaced.

Methods of the present invention provide for the preparation of a customized dental abutment in a manner that reduces the amount of time, labor and cost involved in dental restorative system installation. It has now been realized that taking a series of measurements of the site of tooth replacement allows for the quicker and easier development of a customized dental abutment. Accordingly, methods of the present invention allow for the design and construction of a customized dental abutment based on such measurements.

A method of the invention comprises implanting a dental fixture into a study cast that was previously made of the patient's mouth. This study cast works as a model of the patient's mouth and shows the site of desired tooth replacement as well as its relation to the surrounding teeth. The dental fixture is preferably placed in the study cast using an impression coping device as described in co-owned, co-pending U.S. Ser. No. 08/851,836, incorporated by reference herein.

Once the dental implant fixture is placed in the correct position in the study cast, a preferred method of the invention provides for taking a series of measurements. The measurements include the mesial-distal angle of the site of tooth replacement, the facial-lingual angle of the site, the rotational axis of the fixture, the width of the site, the facial-lingual offset of the site, the mesial-distal offset of the site and the height from the gumline to the top of a dental implant fixture implanted in a patient's mouth. The specific tooth being replaced (e.g., lateral incisor, first bicuspid, etc.) is also determined from its position in the mouth. Based on these measurements a customized dental abutment is fabricated. Other measurements may be used to guide the manufacture of a customized dental abutment. These measurements include the height of the occlusal plane, the gingival profile, and the dimensions (e.g., height, width, etc.) of the adjacent and opposing teeth.

In a particularly preferred method of the invention, a computer program is used to generate a model of the customized abutment based on these measurements. The computer is programmed to generate a model of the customized abutment based on the particular tooth being replaced and on the measurements and tooth and fixture positions. The computer is pre-programmed to contain a series of standard tooth shapes for each type of tooth. The standard shape for the particular type of tooth being replaced is then modified to conform to the measurements taken.

From this customized model, the computer program generates a file from which a wax prototype of the abutment is generated. From the wax prototype, the abutment is built. The technician need only polish and sterilize the abutment before it can be permanently implanted in the, patient's jaw.

Another method of the invention relates to selection of a customized dental abutment from an inventory of such abutments. The inventory is preferably a computer inventory. Measurements such as the mesial-distal angle, the facial-lingual angle, the rotational axis of the dental implant fixture, the width, the facial-lingual offset, the mesial-distal offset, and the height from the gumline to the top of a dental implant fixture implanted in a patient's mouth are taken and compared to the inventory to select a model that most closely replicates the actual tooth being replaced. In addition to these measurements, a determination of the type of tooth (e.g., lateral incisor, first bicuspid, etc.) being replaced is made. Additional measurements may include the height to the occlusal plane and the gingival profile of the tooth being replaced, and the dimensions, including the size, position, orientation and inclination, of the adjacent and opposing teeth of the tooth being replaced.

Methods and materials of the present invention reduce the number of visits that a patient must make to the dentist office, as well as the time and labor required to complete a dental restoration. The present invention allows for the patient to make as few as three visits to a dentist's office. The first visit would entail making the study cast for use in fabricating the abutment. At the second visit, the dental implant fixture is installed and an impression of the position of the dental implant fixture and its relation to the natural dentition is made. The study cast and impression are then used to fabricate a customized dental abutment, as described above. No further modifications to the abutment are necessary using the above process, so the abutment and crown can be installed at the third and final visit to the dentist's office. The abutment is fabricated to eliminate the need for a healing abutment, as described in co-owned, co-pending U.S. Ser. No. 08/372,323, incorporated by reference herein.

The invention will be understood further upon consideration of the following drawings, description and claims.

DESCRIPTION OF THE DRAWINGS

Like reference characters in the respective drawn figures indicate corresponding parts.

DETAILED DESCRIPTION OF THE INVENTION

Figure 1:
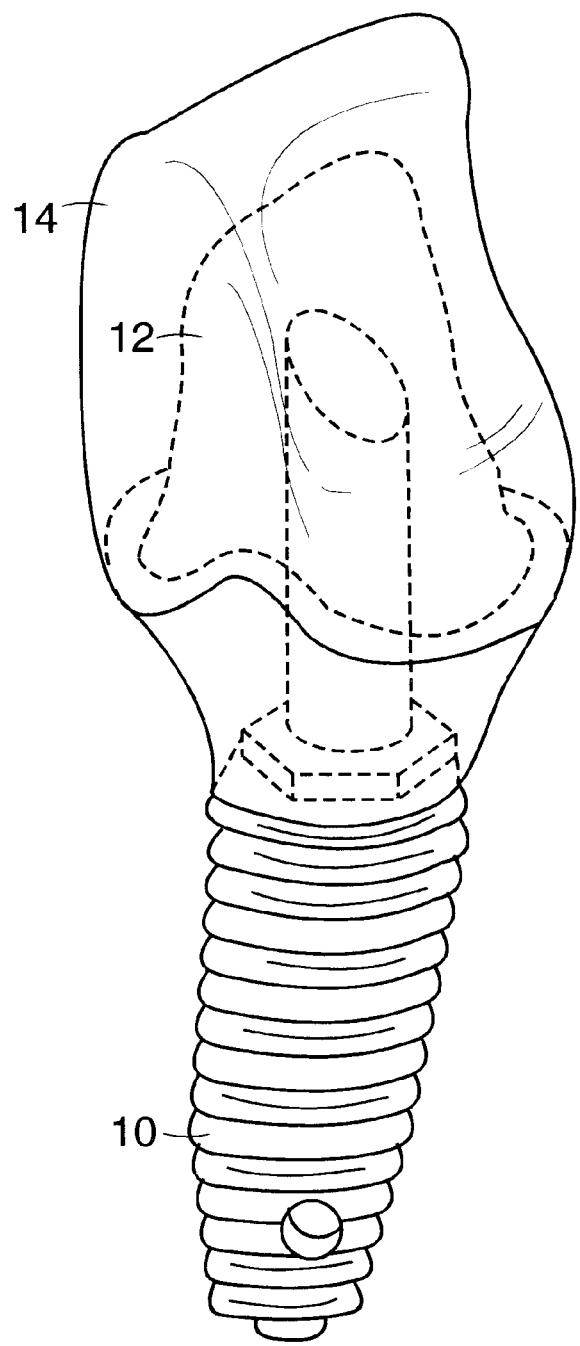
FIG. 1 shows a complete dental restorative system including dental implant fixture 10, customized abutment 12, and crown 14.

The present invention relates to methods and materials for use in dental restorative systems. A dental restorative system replaces a tooth in a patient's mouth. A dental restorative system is shown in FIG. 1 and comprises a dental implant fixture 10, which is implanted in the mouth of a patient at the site of desired tooth replacement. The dental implant fixture anchors the other components of the system in proper position and alignment with respect to the natural dentition. The system also includes an abutment 12, which is installed in the dental implant fixture and over which the crown 14 is affixed. The crown is the visible portion of the restorative system, so it must be contoured and shaped to look like a natural tooth. The underlying abutment should also be fabricated to match the size, shape and contour of the replaced tooth.

More specifically, present invention provides customized dental abutments for use in dental restorative systems and methods of preparing or selecting such abutments. An abutment of the invention is fabricated based on the application of a series of measurements taken at the site of tooth replacement to a standard shape for the type of tooth being replaced.

Figure 2A:
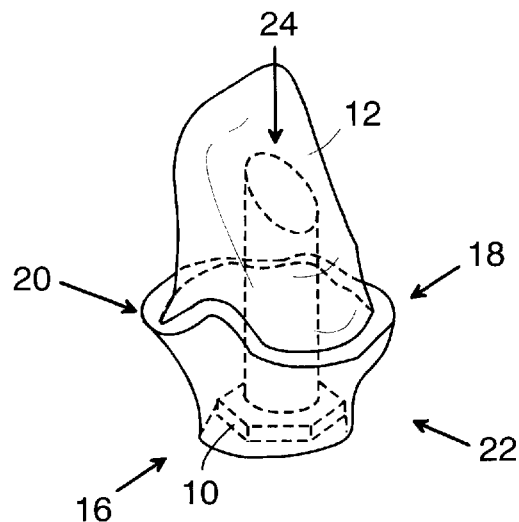
FIG. 2A shows the various faces of an abutment of the invention installed in a dental implant fixture.
Figure 2B:
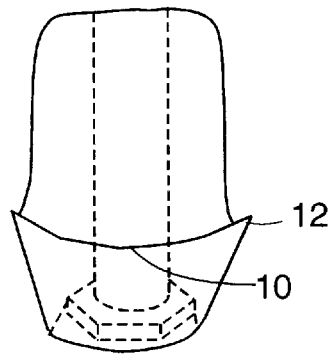
FIG. 2B shows a facial view of the abutment of FIG. 1A.
Figure 2C:
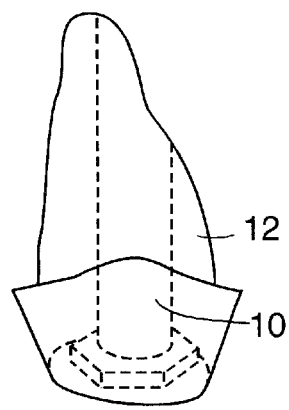
FIG. 2C shows a side (mesial or distal) view of the abutment of FIG. 1A.

A preferred abutment of the invention is shown in FIG. 2A. A series of measurements is taken with respect to the different faces of the abutment 12. FIG. 2A shows the mesial agent 16 and the distal agent 18 of a typical abutment. The mesial agent is the side facing the focial midline and the distal capect is the side facing away from the facial midline. A side view of an abutment is also shown in FIG. 2C, and this figure represents either a distal or a mesial face.

FIG. 2A also shows the facial agent 20 and lingual agent 22 of an abutment. The facial agent of the abutment faces toward the cheeks or lips, and the lingual agent of the abutment faces toward the tongue. A view of the facial agent of an abutment is also shown in FIG. 2B. Finally, FIG. 2A also shows an occlusal plane 24. The occlusal plane is the surface of the tooth that comes in contact with the surfaces of opposing teeth.

In methods of the invention, the foregoing measurements are made with respect to their orientation to an implanted dental fixture. Such measurements are used to fabricate a customized dental abutment of the invention. Prior to the taking of such measurements, however, some preparative actions should be taken by the dentist, prosthodontist and/or oral surgeon. For example, a study cast of the patient's existing teeth is made. Then, a dental fixture, such as that manufactured by Life Core, is implanted in a bore hole made in a patient's jaw at the site of desired tooth replacement. The implant site is surgically prepared by drilling into the jawbone after the gingival tissue surrounding the point of insertion of the implant has been retracted. An implant fixture may comprise a male hexagonal interface at its exposed end, as well as a hollow bore, which is open from the exposed end of the fixture and extends into the fixture.

Figure 3:
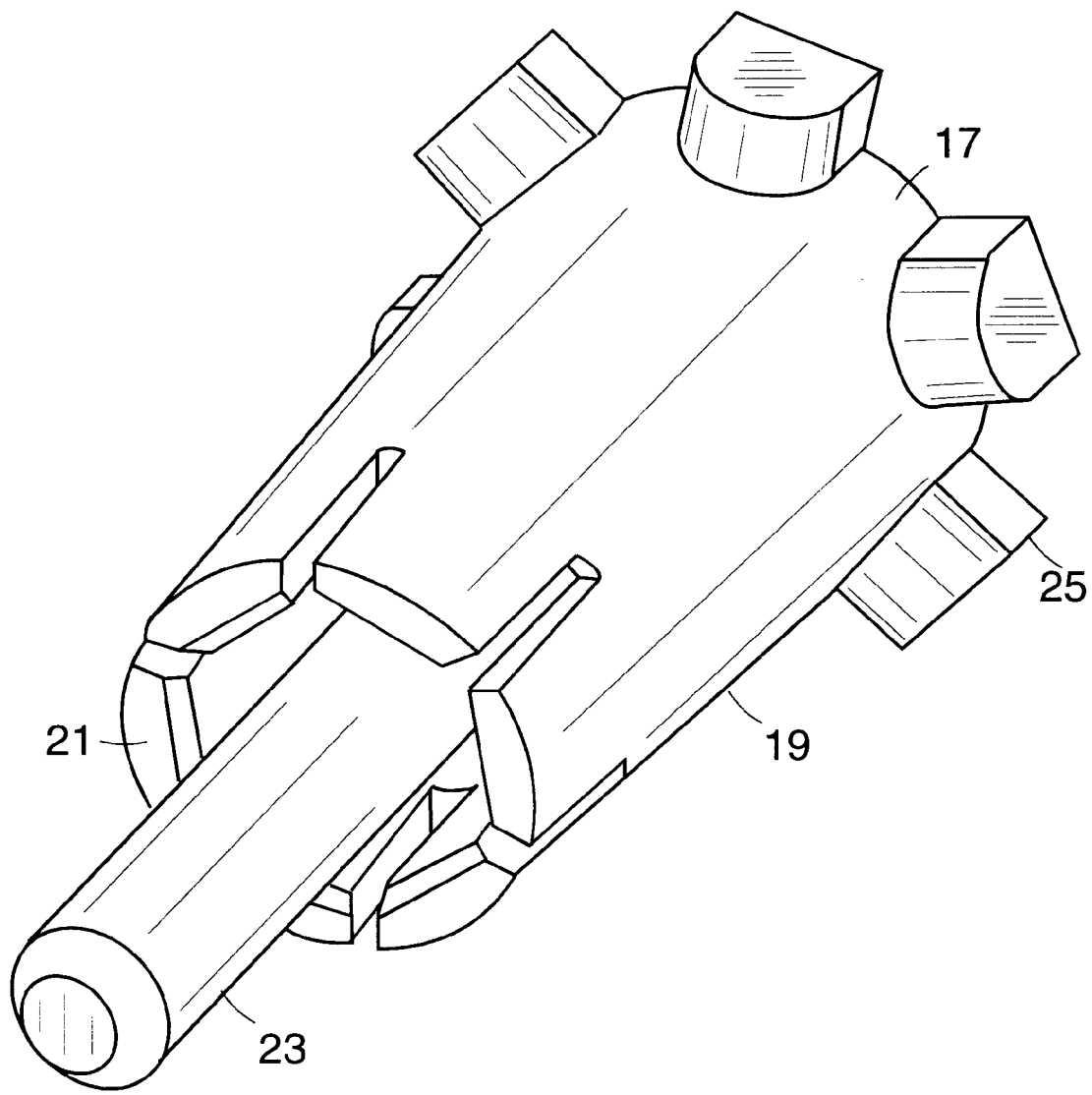
FIG. 3 shows an impression coping device for use in fabricating customized dental abutments of the invention.

An impression of the positional and rotational alignment of the dental fixture with respect to the natural dentition must then be taken. The impression ensures that the abutment and crown will have the proper alignment to fit into the natural dentition. An impression is preferably made through the use of an impression coping device as shown in FIG. 3, and as described in co-owned, co-pending U.S. Ser. No. 08/851, 836, incorporated by reference herein. Such an impression coping device comprises a head 17 having a first end 19 that is preferably castellated so that it releasably attaches to a dental implant fixture. The castellated end comprises a plurality of axially extending, radially resilient fingers 21 that deflect as they are friction fitted over a mating surface, such as the male hexagonal interface described above, of a dental implant fixture. The coping device also has a guide stem 23, which fits into the hollow bore of the dental implant fixture.

A coping device as described above is fitted into the dental implant fixture and an impression material, such as, for example, polyether siloxane or polyvinyl siloxane, is poured over the coping device and surrounding teeth. Upon curing, an impression of the natural dentition and their positional and rotational alignment with respect to the dental implant fixture is preserved. A second end of the coping device also contains one or more radially arranged flanges 25 to anchor the impression molding material to the coping device and facilitate its removal from the mouth upon curing. The skilled artisan is aware that other coping devices for making impressions are available and may be used to make an impression as described above.

After the study cast and impression are completed, methods of the invention provide for the fabrication of a customized dental abutment from the study cast and impression. A dental implant fixture is first implanted in the study cast at the site of desired tooth replacement. The impression is used to guide the proper rotational and positional alignment of the dental implant fixture in the study cast. The impression coping device containing the attached impression material is attached to an analog fixture, which is then cast in the study cast. The space surrounding the analog fixture is then filled and allowed to cure so that the analog fixture becomes part of the study cast, thus maintaining the proper positional and rotational alignment of the dental fixture with respect to the patient's natural dentition.

Figure 4A:
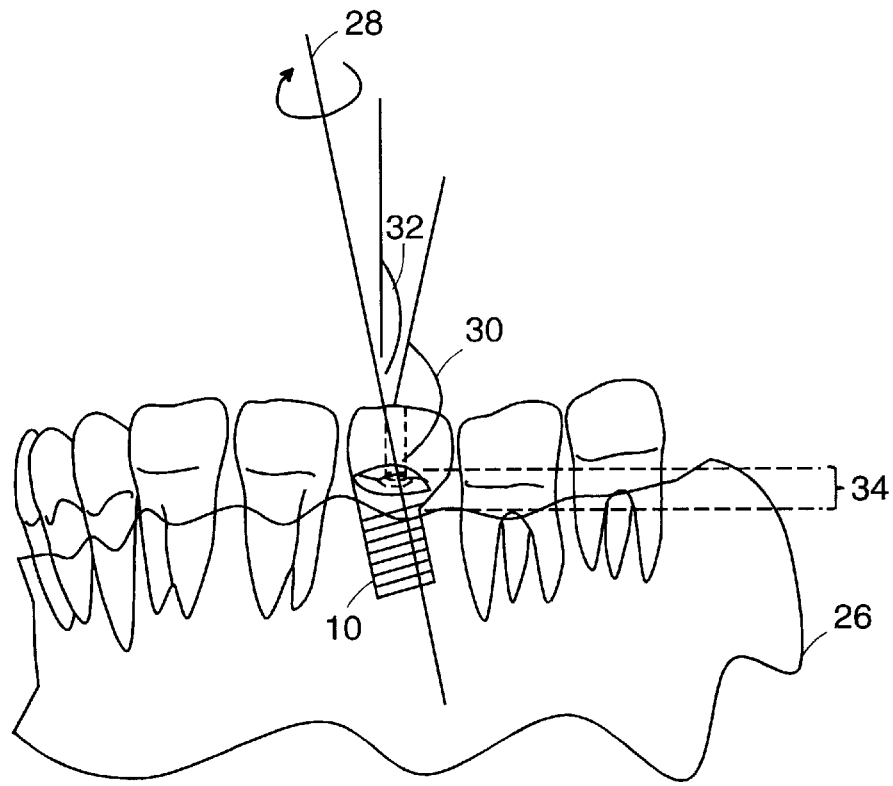
FIG. 4A illustrates some of the various measurements taken in order to fabricate a customized dental abutment of the invention.

After the analog fixture is properly placed in the study cast, measurements may be made. Measurements may be taken by several means including, but not limited to, a stent, a mold of the teeth, an optical device, or other measuring instrument. FIG. 4A illustrates some of the measurements that are taken. The rotational axis of the fixture 10 is shown as 28. The mesial-distal angle with respect to this axis is shown as 30, and the facial-lingual angle with respect to this axis is shown as 32. The height from the gumline to the top of the dental implant fixture is shown as 34.

Figure 4B:
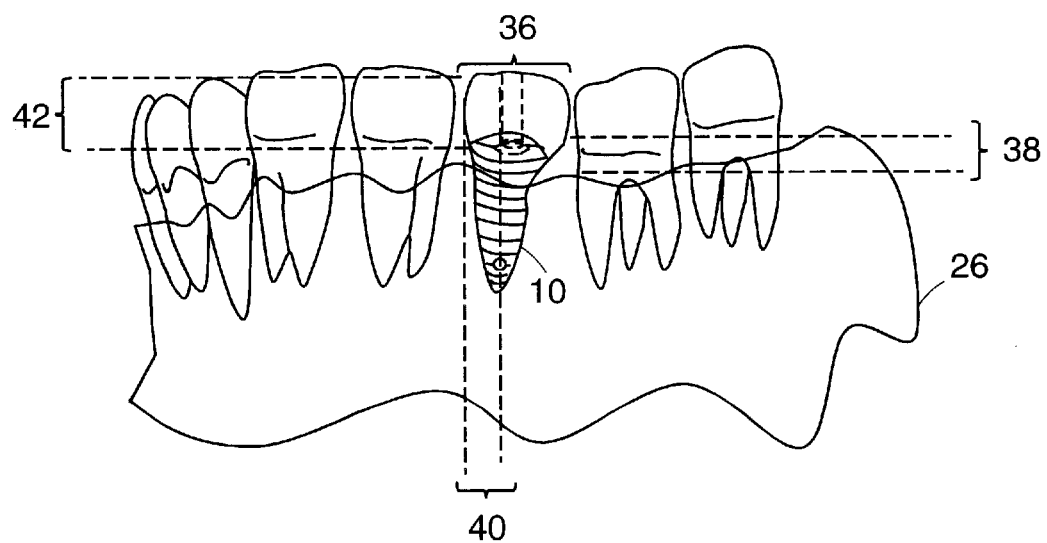
FIG. 4B illustrates some of the various measurements taken in order to fabricate a customized dental abutment of the invention.

Other measurements are shown in FIG. 4B. The width of the gap between the teeth adjacent the tooth to be replaced is shown at 36. The facial-lingual offset, or the distance from the mid-point of the dental implant fixture to the facial surface of the tooth, is shown at 38. The mesial-distal offset is shown at 40. The mesial-distal offset corresponds to one half of the difference in the distances measured from the fixture to each adjacent tooth. For example, if the distance from the dental implant fixture to the first adjacent fixture is x and the distance from the dental implant fixture to the second adjacent tooth is y, the mesial-distal offset is (x-y)/2. Finally, the height to the occlusal plane, or the distance from the gumline to the surface of the tooth that contacts opposing teeth, is shown at 42.

Measurements of any or all of these parameters are taken to guide the fabrication of an abutment that closely approximates the size, shape and position of the tooth being replaced. In an embodiment of the invention, the mesial-distal angle, facial-lingual angle, rotational axis of a dental implant fixture implanted at the site of desired tooth replacement, width, facial-lingual offset, mesial-distal offset and height from the gumline to the top of a dental implant are all measured. A determination of the type of tooth being replaced (e.g., lateral incisor, first bicuspid, etc.) is also made. From these measurements, a customized abutment of the invention may be prepared. In a preferred embodiment, other measurements, such as the height to the occlusal plane, gingival profile (i.e., profile of gumline with respect to the tooth) and dimensions (e.g., width, height to occlusal plane, etc.) of the adjacent and opposing teeth are also taken prior to preparing the customized abutment.

In a preferred embodiment, a model of a customized dental abutment of the invention is generated by a parametrix solid modeling system computer program, such as SolidWorks™ manufactured by SolidWorks, Inc. (Concord, Mass.). A series of average measurements for each of the various types of teeth are used to pre-program the computer to generate baseline models. Such average measurements may be found, for example, in Wheeler, *Dental Anatomy, Physiology and Occlusion* (5th ed. 1974), incorporated by reference herein.

Figure 5A:
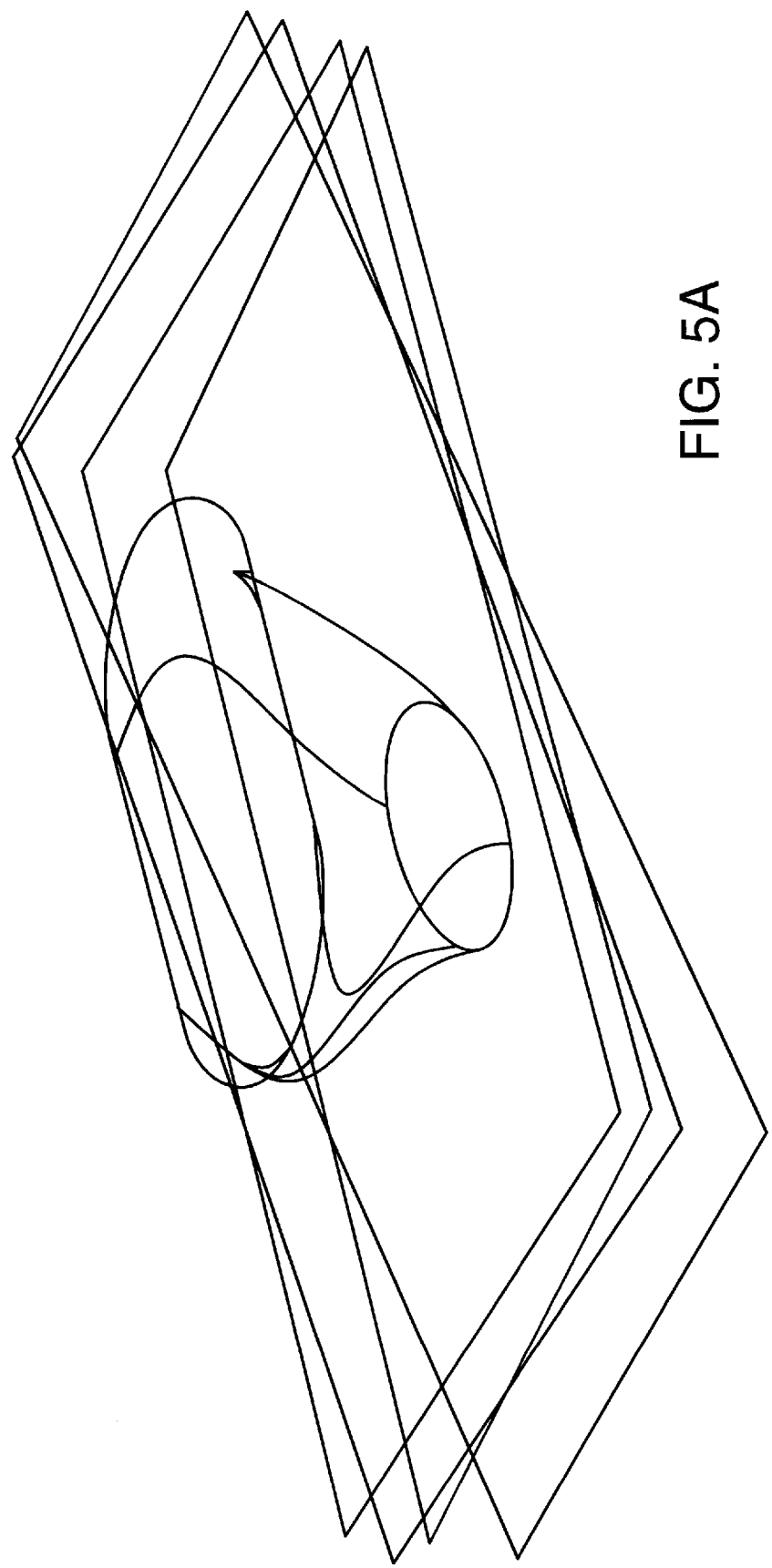
FIGS. 5A–5H illustrate the various stages undergone in designing a computer model of a standard tooth shape for use in building a customized dental abutment of the invention.
Figure 5B:
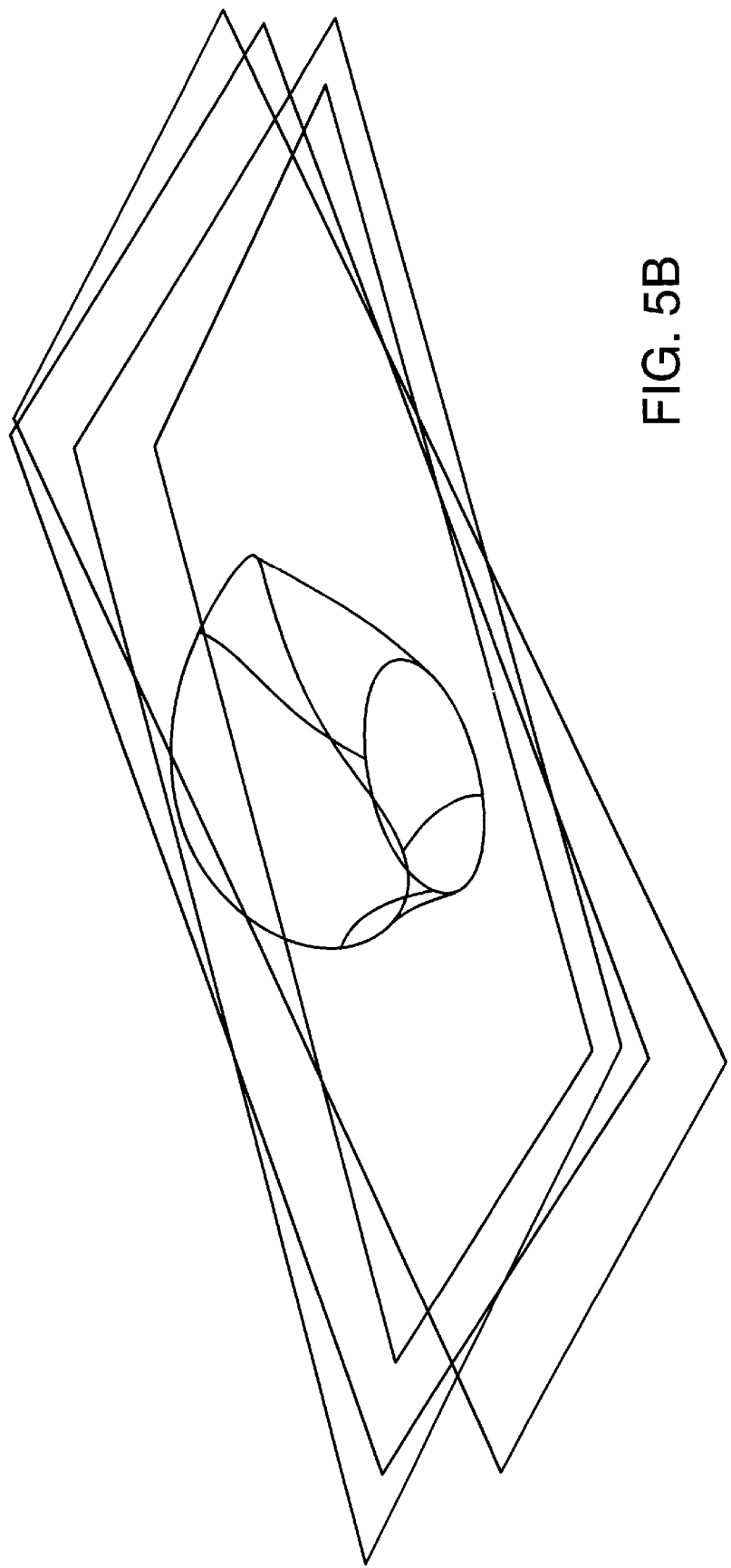
Figure 5C:
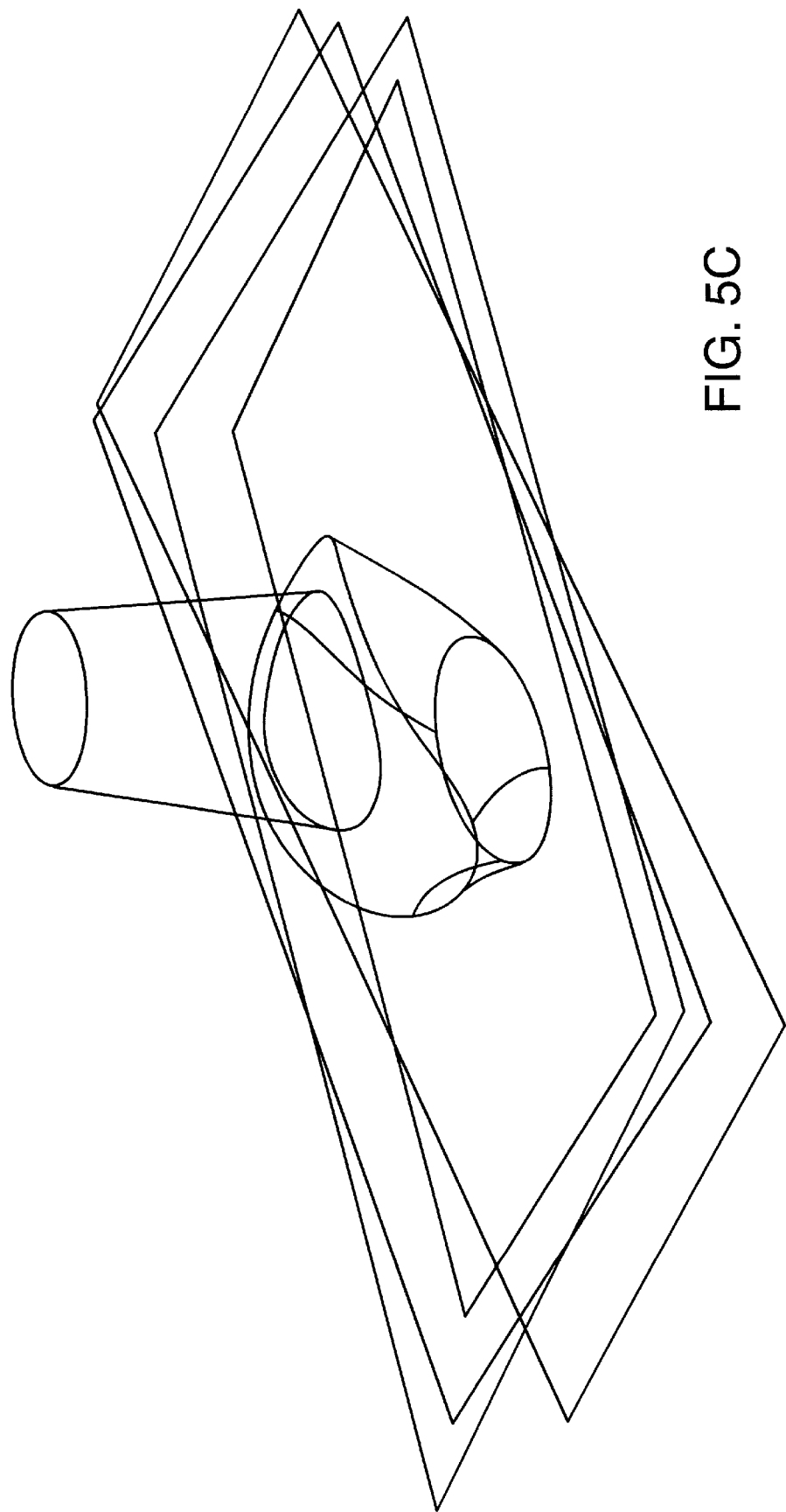
Figure 5D:
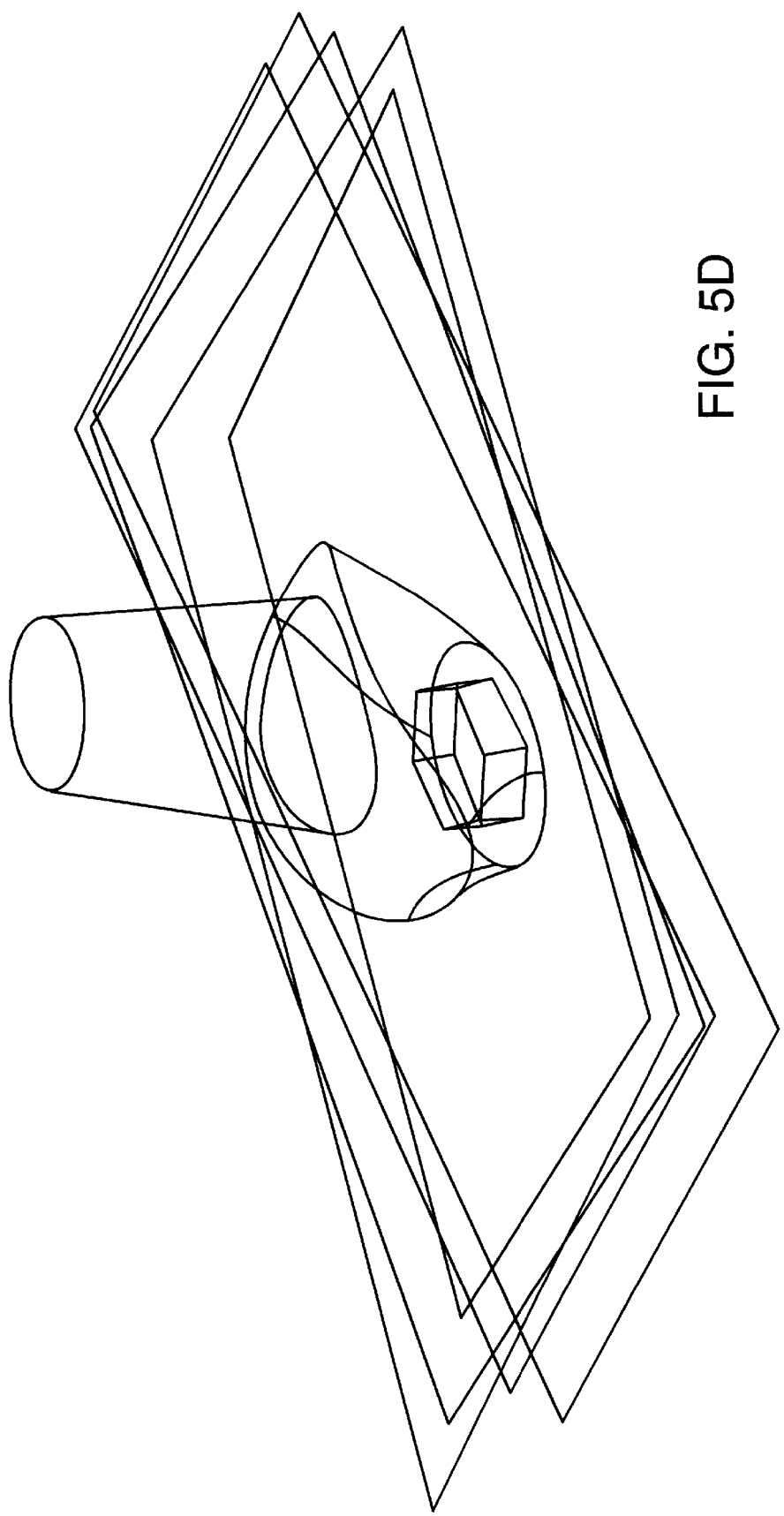
Figure 5E:
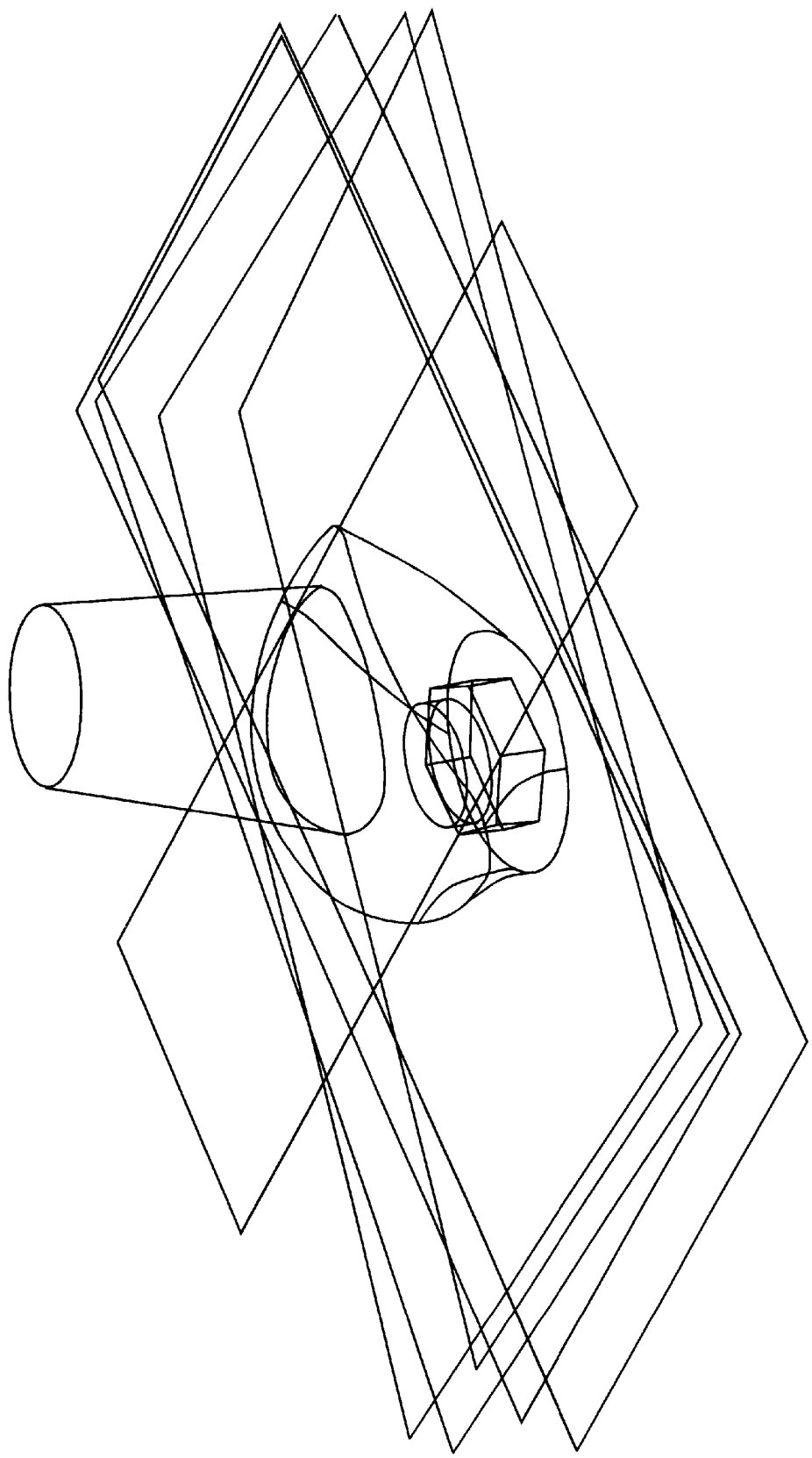
Figure 5F:
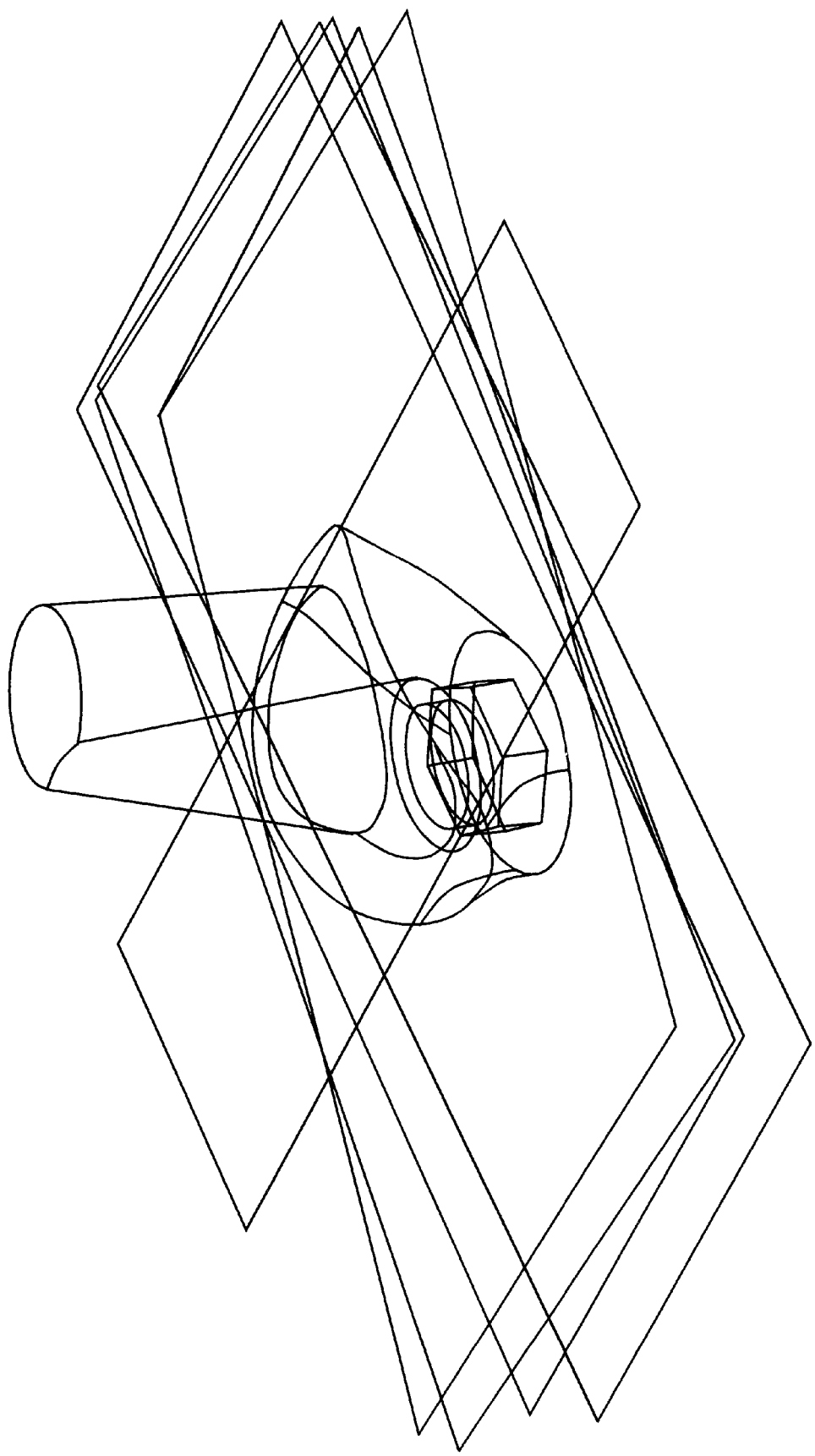
Figure 5G:
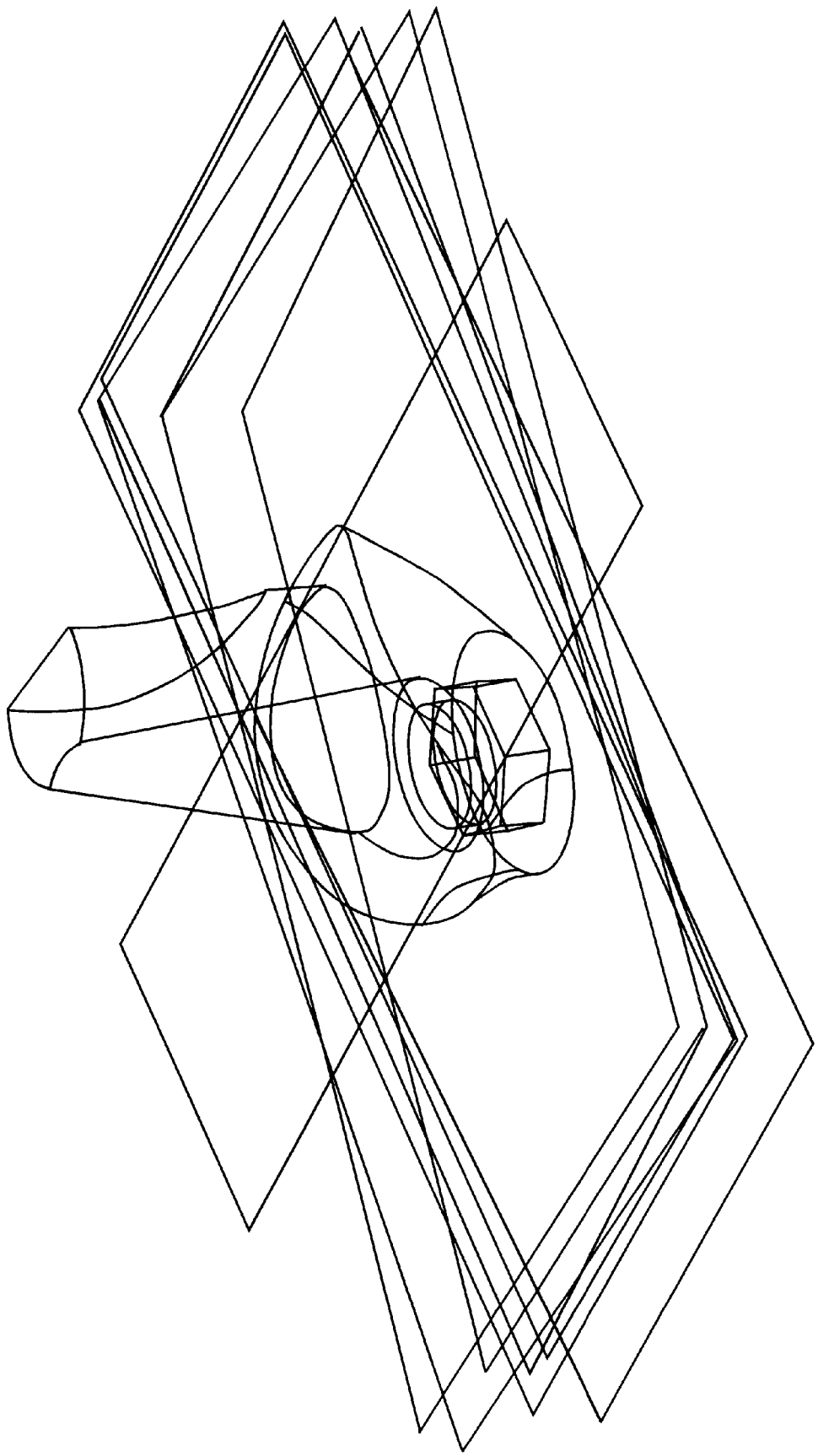
Figure 5H:
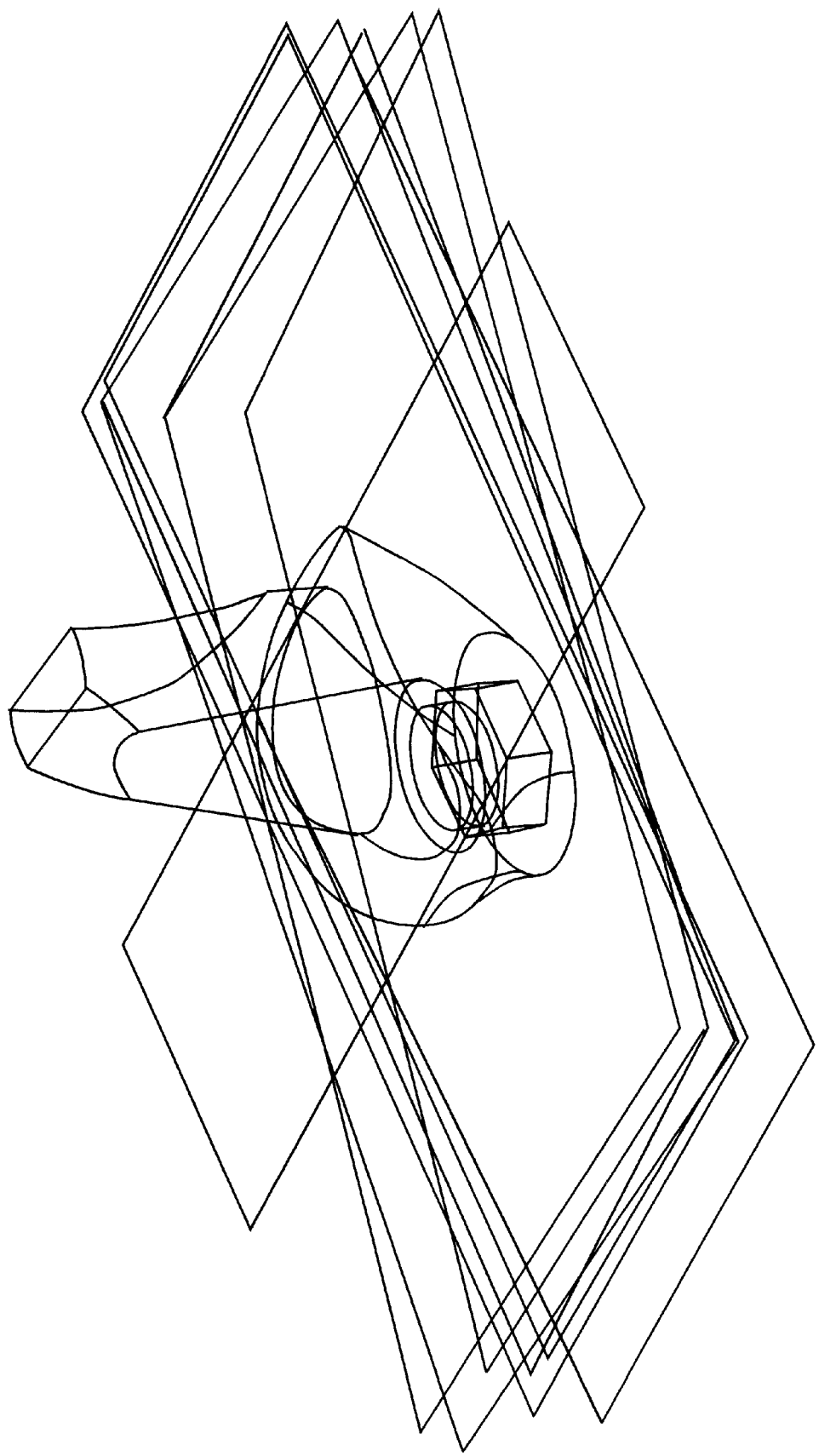

A standard shape is generated for each of the various types of teeth. The standard shape represents the average tooth shape for the type of tooth being replaced. The collection of standard shapes represents the inventory from which a Customized abutment is contoured. For example, to generate a standard shape for a right maxillary lateral incisor the shape shown in FIG. 5A is first drawn using the computer program. Points in each plane of a three-dimensional co-ordinate system are added and connected until the shape approximates that shown in FIG. 5A. The top of this shape is then removed along one plane of the model to give the shape shown in FIG. 5B. To this shape is then added a frusto-conical shape as shown in FIG. 5C. The interface between the abutment and the dental implant fixture is then built into the model. As shown in FIG. 5D, the interface may have a hexagonal shape. Further refinements of the interface are shown in FIG. 5E. Finally, an opening in the abutment model must be made for insertion of the mechanism that secures the abutment to the dental implant fixture. This step is shown in FIG. 5F. This model may then be modified using the parametrix solid modeling system computer program to add contours and other variations in the shape so that it more closely approximates the contours of a natural tooth as shown in FIGS. 5G and 5H. Other methods of generating a similar model by use of parametrix solid modeling system computer program are possible.

The measurements taken at the site of desired tooth replacement and the determination of the type of tooth being replaced are then entered into the modeling program. The program then compares the measurements taken of the site to the pre-programmed standard shapes for the type of tooth being replaced. If a particular measurement differs from the average measurement for that tooth, the computer modifies the standard shape to conform to the measurement taken of the site of desired tooth replacement. The computer program also scales the model to conform to the measurements of the site of desired tooth replacement that are entered. In other words, the computer modifies the model in accordance with the measurements that are entered while maintaining proper geometry of the model.

The model generated by the computer is then used to create a prototype of the customized abutment. A prototype, preferably made of wax, of the abutment may be created, for example, on a Sanders Prototype, Inc. Model Maker 6 Pro® rapid prototyping machine. From this prototype a cast of the abutment is made. The abutment is then fabricated from this cast, polished and sterilized, resulting in the customized dental abutment of the invention.

Methods of the invention also relate to selection of a customized dental abutment from an inventory of abutments. The inventory is preferably a pre-programmed computer inventory. A computer program, such as that described above, is used to generate an inventory of abutments of various parameters by creating versions of the type of tooth which vary according to the measurements described above. By taking measurements of the site of desired tooth replacement and determining the type of tooth to be replaced, a model of an abutment can be selected from the inventory. The measurements and tooth type are entered into the computer pre-programmed with the inventory of abutments. The measurements are compared to the available models for that tooth type, and a model that most closely approximates the measurements is selected. This model is then used to generate a prototype from which a customized dental abutment may be cast, as described above.

A customized dental abutment so fabricated is then sent to the dental practitioner for installation into the dental implant fixture implanted into the patient's jawbone. After the site of the implanted dental fixture is healed, the customized dental abutment of the invention is secured in place in the dental implant fixture by, for example, screwing it into place in the dental implant fixture. The use of a healing abutment is not required as described in co-owned, co-pending U.S. Ser. No. 08/372,323, incorporated by reference herein. A crown that approximates the size and color of the natural dentition is attached to the abutment with an adhesive and/or a lateral set screw. A dental technician sculpts the crown with reference to the previously-prepared analog fixture and abutment. The crown is sculpted from, for example, wax or ceramic. The skilled artisan is aware that numerous methods may be used to sculpt a crown from an analog fixture and abutment.

An dental restoration is therefore performed without the high number of office visits required by standard methods, and without the amount of cost and labor involved in standard methods. Additional aspects and advantages of the invention are apparent upon consideration of the foregoing. Accordingly, the scope of the invention is limited only by the scope of the appended claims.

What is claimed is:

1. A method of selecting a dental abutment from an inventory of dental abutments, comprising the steps of:

(a) determining a series of measurements at the site of tooth replacement for a tooth being replaced, said measurements comprising a mesial-distal angle, a facial-lingual angle, a rotational axis of a dental implant fixture implanted at a site of desired tooth replacement, a width, a facial-lingual offset, a mesial-distal offset, and a height from the gumline to the top of a dental implant fixture implanted in a patient's mouth for the specific tooth being replaced;

(b) determining a type of tooth being replaced; and (c) selecting an abutment based on said determinations.

2. The method of claim 1, wherein said measurements further comprise a height to the occlusal plane and a gingival profile of the tooth being replaced, and the dimensions, including the size, position, orientation and inclination, of adjacent and opposing teeth of the tooth being replaced.

3. The method of claim 1, wherein said inventory is a computer inventory.

* * * * *